United States Patent [19]
Caudill et al.

[11] Patent Number: 6,107,811
[45] Date of Patent: Aug. 22, 2000

[54] COUPON MONITOR FOR CATHODIC PROTECTION SYSTEM

[75] Inventors: Dan L. Caudill, Grove City; Neil G. Thompson, Dublin; Kurt M. Lawson, Sugar Grove, all of Ohio

[73] Assignee: CC Technologies Laboratories, Inc., Dublin, Ohio

[21] Appl. No.: 09/023,405

[22] Filed: Feb. 12, 1998

[51] Int. Cl.[7] .................................................. G01R 27/08
[52] U.S. Cl. .......................................... 324/713; 324/693
[58] Field of Search .................................. 324/425, 71.1, 324/71.2, 693, 713; 204/404, 196.2, 196.3, 196.5, 196.06

[56] References Cited

U.S. PATENT DOCUMENTS

| | | | |
|---|---|---|---|
| 4,725,778 | 2/1988 | Brown | 324/263 |
| 4,752,360 | 6/1988 | Jasinski | 204/1 T |
| 4,863,572 | 9/1989 | Jasinski | 204/1 T |
| 5,144,247 | 9/1992 | Speck | 324/425 |
| 5,216,370 | 6/1993 | Bushman et al. | 324/425 |
| 5,370,776 | 12/1994 | Chen | 204/153 |
| 5,469,048 | 11/1995 | Donohue | 324/71.1 |
| 5,728,943 | 3/1998 | Colter, Jr. et al. | 73/799 |
| 5,814,982 | 9/1998 | Thompson et al. | 324/71.1 |
| 5,854,557 | 12/1998 | Tiefnig | 324/700 |

*Primary Examiner*—Safet Metjahic
*Assistant Examiner*—Russell M. Kobert
*Attorney, Agent, or Firm*—Frank H. Foster; Kremblas, Foster, Millard & Pollick

[57] ABSTRACT

An automated coupon monitor for detecting the electrical parameters associated with a pipe, a coupon and a reference electrode utilized with a cathodic protection system. A voltage detector circuit has its output applied to a pair of sample and hold circuits, one for recording $E_{OFF}$ and the other for recording $E_{ON}$. Series connected between the coupon and the pipe is a zero resistance current detector circuit and an interrupter switch for measuring the pipe-coupon current and periodically interrupting that current to permit measurement, sampling and storing of $E_{OFF}$. The sample and hold circuits and the interrupter switch are controlled by a microprocessor controller. The circuit provides DC level outputs which can be easily read by a digital multimeter or stored in a data logger for subsequent reading or transmission to another location.

20 Claims, 6 Drawing Sheets

COUPON MONITOR FOR CATHODIC PROTECTION SYSTEM

BACKGROUND OF THE INVENTION

1. Field of the Invention

This invention relates generally to cathodic protection systems for protecting metal objects, which are buried in soil, from corrosion. The invention more particularly relates to a circuit for monitoring electrical parameters associated with the buried object and a coupon and reference electrode which are conventionally installed to provide information about the effectiveness of the cathodic protection.

2. Description of the Related Art

Metal structures such as pipes and tanks, which are buried in soil, are naturally subjected to an electro-chemical corrosion process in their underground environment. The metal structure acts as an electrode and the soil an electrolyte so that an electrolytic cell is formed causing corrosion of the buried structure.

Cathodic protection has commonly been applied to such buried objects in order to counteract and thereby mitigate the electrochemical corrosion reaction. Such cathodic protection systems are monitored in order to determine a level of cathodic protection which is sufficient to adequately mitigate the corrosion of the buried metal object. The level considered sufficient is determined by industry accepted standards, based upon a measurement of the potential difference between the buried object and a standard reference electrode also placed in contact with the soil electrolyte.

One problem with measuring this potential arises from potential differences in the soil resulting from currents through the distributed resistance of the soil. It is necessary to turn off the cathodic protection in order to eliminate the voltage drop arising from the cathodic protection current flowing through the distributed resistance of the soil. However, not only does this interrupt the protection, but it does not eliminate additional voltage drops in the soil which result from stray currents from underground power sources, such as transit systems which cannot be turned off. Additionally, long buried pipelines commonly have a series of several cathodic protection systems spaced along the pipeline. Elimination of the IR drop through the soil from the neighboring cathodic protection systems would require that all cathodic protection systems be turned off during measurement of the pipe to reference electrode voltage.

In order to avoid these problems, coupons are used to monitor the level of cathodic protection on buried metal objects. A coupon is a bare metal electrode having substantially the same metallurgical, and therefore electrochemical, attributes as the buried metal object. The coupon is buried in the soil near the buried metal object so that it is subjected to the same corrosive effects and the same cathodic protection as the buried metal object. Consequently, the coupon is used to simulate the buried metal object and potential difference measurements are taken between the coupon and the reference electrode. This allows the application of cathodic protection to the buried metal object to continue uninterrupted, while only the cathodic protection to the coupon is interrupted for purposes of taking measurements. The coupon reference potential therefore simulates the potential of a coating defect or holiday on the buried metal object.

In order to evaluate such a cathodic protection system there are three electrical parameters which are commonly measured. The first is the electrical current between the coupon and the pipe, the second is the voltage, $E_{ON}$, between the pipe and the reference electrode when current is flowing between the coupon and the pipe, and the third is the voltage, $E_{OFF}$, between the coupon and the reference electrode at some standard time delay after the coupon-pipe current is interrupted.

These electrical parameters are conventionally measured by an individual technician travelling into the field and connecting a strip chart instrument to the coupon, pipe and reference electrode connections provided at the site of the coupon and reference electrodes. The technician connects the instruments, takes readings and interrupts the electrical connection between the pipe and the coupon to obtain a measurement of $E_{OFF}$. The technician must then examine the strip chart and visually determine the appropriate values to record.

One difficulty with such manual measurement is that the values fluctuate with time. The technician must follow the time line of the strip chart for the time delay of the standard test utilized by the particular company responsible for cathodic protection, and estimate the appropriate $E_{OFF}$ voltage by visual inspection of a meandering line on a strip chart. This manner of measurement is not only inherently inaccurate because of its dependence upon visual inspection and mental interpolation, but also requires training and skill on the part of the technician who is going into the field to make the measurements.

It is therefore an object and feature of the invention to provide a coupon monitor which is capable of making automated measurements of these corrosion coupon parameters.

It is a further object and feature of the invention to allow complex, interrupted potential and current measurements to be easily detected and recorded in the field using a simple digital voltmeter giving a direct reading of the detected potentials and current, so that these can be reliably recorded by persons who do not possess as much skill as currently required.

It is a further object and feature of the invention to provide a coupon monitor which can be attached to a data acquisition system so that a time sequence of parameters can be stored, subsequently downloaded, and utilized by a digital data processing system.

SUMMARY OF THE INVENTION

The invention is a circuit for monitoring electrical parameters associated with a buried metal object, a coupon and a reference electrode. A voltage detector circuit is connected to detect the voltage between the reference electrode and the coupon and preferably also the voltage between the reference electrode and the buried object. A current detector circuit is connected for detecting the current between the object and the coupon. At least one sample and hold circuit is connected to the outputs of these detector circuits for sampling and storing their measured values of voltage and current. A current interrupting switch is interposed in series with the current detector for periodically interrupting the pipe-coupon current. The interrupter switch, as well as the sample and hold circuits, are controlled by a controller circuit. Preferably, there are three sample and hold circuits, two for sampling and holding the output of the voltage detector and the other for sampling and holding the output of the current detector. Additionally, it is preferred that a low pass filter be interposed between each detector circuit and the sample and hold circuit connected to its output, and that the current detector circuit also be capable of maintaining a substantially zero voltage between the object and the coupon.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the word connected or terms similar thereto are often used. They are not limited to direct connection but include connection through other circuit elements where such connection is recognized as being equivalent by those skilled in the art. In addition, many circuits are illustrated which are of a type which perform well known operations on electronic signals. Those skilled in the art will recognize that there are many, and in the future may be additional, alternative circuits which are recognized as equivalent because they provide the same operations on the signals.

DESCRIPTION OF THE PREFERRED EMBODIMENT

Figure 1:
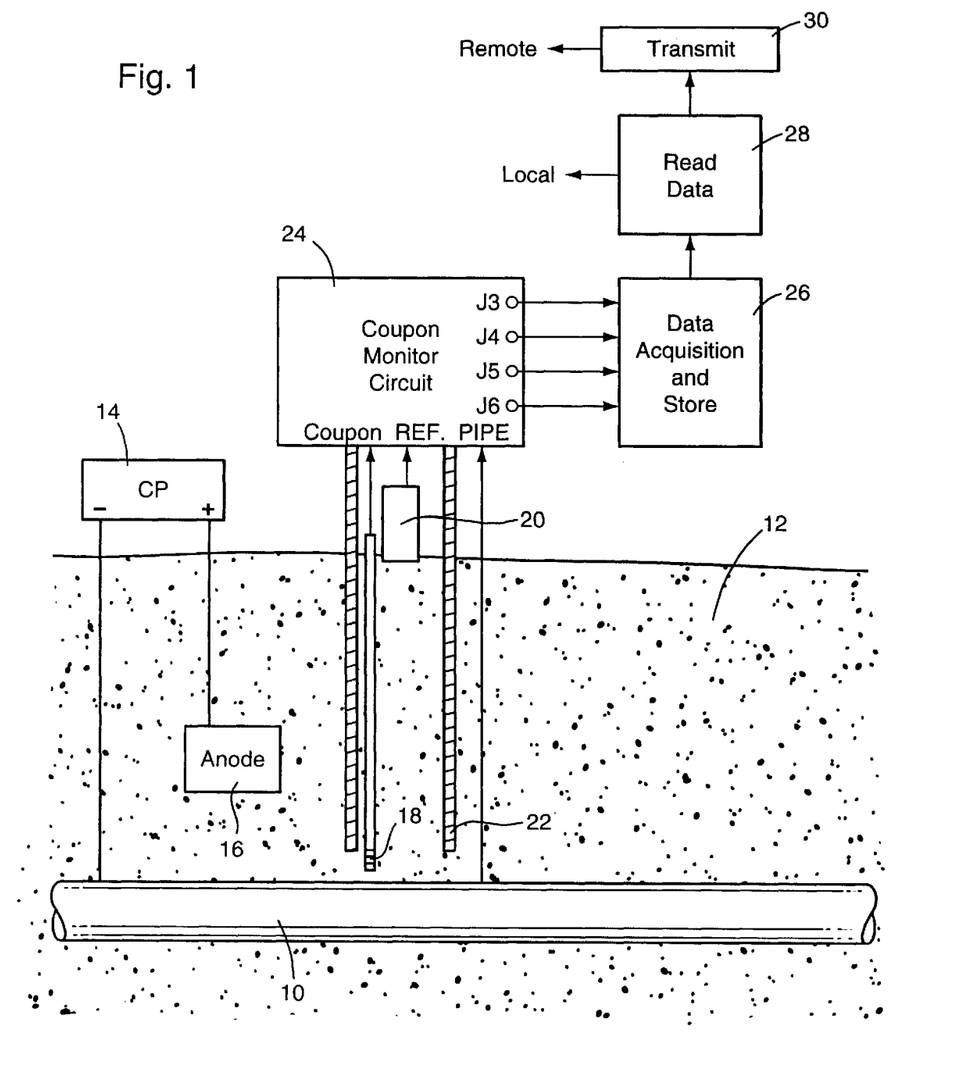
FIG. 1 is a diagram in vertical section illustrating the connection of the present invention to a cathodically protected structure, a coupon and a reference electrode.

FIG. 1 illustrates a pipe 10 buried in a soil 12 and protected by a cathodic protection system, including a DC power supply 14 electrically connected to the pipe 10 and to a buried anode 16. For monitoring the level of cathodic protection, a coupon 18 is buried in the soil 12 near the pipe 10 and a reference electrode 20 is also positioned in electrical contact with the soil 12. The coupon 18 and reference electrode 20 may be of conventional structure, or may be positioned within a surrounding, non-conductive, cylindrical tube 22 in accordance with an invention which is the subject of a separate patent application.

The present invention is a coupon monitor circuit 24 electrically connected to the pipe 10, the coupon 18, and the reference electrode 20 at suitable input terminals. Output data from the coupon monitor circuit 24 appears at output terminals J3, J4, and J5, referenced to ground terminal J6, in the form of DC voltage levels representing, and preferably proportional to, the pipe-coupon current, the pipe/reference voltage, $E_{ON}$, and the coupon/reference voltage, $E_{OFF}$, measured a predetermined time interval after the pipe-coupon current is interrupted.

This output data may be read by simply applying one probe of a digital multimeter or voltmeter to output terminal J6 and the other probe sequentially in turn to terminals J3, J4, and J5. Alternatively, however, these output data may be applied to a conventional data acquisition and storage device 26 where they may be stored for later transfer through a data reading circuit 28 for local readings and/or to a transmitter 30 for wire line or wireless transmission to an area remote from the coupon monitor circuit 24.

Figure 2:
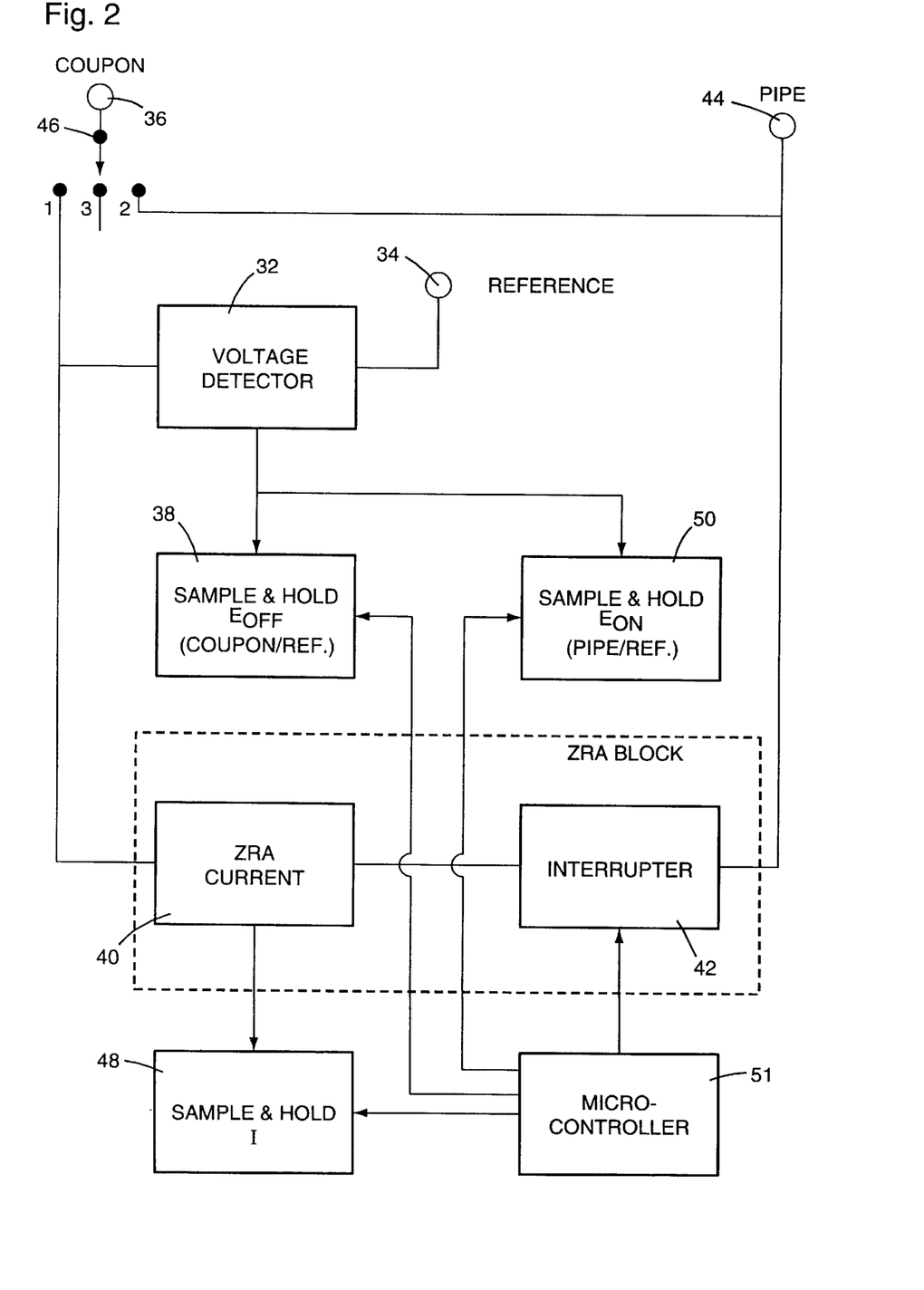
FIG. 2 is a block diagram illustrating the preferred embodiment of the invention.

FIG. 2 is a block diagram illustrating the basic components of the coupon monitoring circuit of the present invention. The voltage detector circuit 32 has its voltage detecting input connected between the terminal 34, which is connected to the reference electrode 20, and the terminal 36, which is connected to the coupon 18. The output of the voltage detector circuit 32 is applied to sample and hold circuits 38 and 50, which are capable of sampling and storing the output of the voltage detector circuit 32. This output voltage represents the coupon/reference voltage.

The monitoring circuit also has a zero resistance current detector circuit 40 series connected to a current interrupter switch 42. The series current detector circuit 40 and interrupter switch 42 are connected between the coupon terminal 36 and the terminal 44 connected to the pipe. A single pole, triple throw, mode switch 46 is interposed in the series connection between the pipe terminal 44 and the coupon terminal 36. It is positioned at position 1 for normal monitoring operation. Position 2 represents an inoperative state of the coupon monitoring circuit which maintains the pipe-coupon connection and cathodic protection of the coupon. In position 2 the pipe and coupon are maintained at the same potential by conduction through the circuit. In position 3, both the monitoring circuit and cathodic protection of the coupon are inactive. Position 3 is utilized, for example, after installing a new coupon because it is desirable that the coupon become settled and tightly surrounded by the soil in the same manner as the pipe. Furthermore, a new coupon will generally have a clean, uncorroded surface, and consequently will be electro-chemically different than a previously installed pipe, even though the metals are identical. Therefore, connecting a newly installed coupon to an older pipe may cause galvanic action or other problems. As a result, the mode switch is switched to position 3, while the coupon settles for a period of time on the order of a month or two before being switched to position 1 or 2.

A sample and hold circuit 48 is also connected to the output of the current detector circuit 40 for sampling and storing the output of the current detector circuit 40. The current interrupter switch 42 periodically interrupts the current through the current detecting circuit 40 to permit measurement of the coupon/reference voltage, $E_{OFF}$, a selected time period after the current interrupter switch 42 is opened to prevent current flow through the zero resistance current detector circuit 40.

A third sample and hold circuit 50 is also connected to the output of the voltage detector 32. Three sample and hold circuits are used to assure that all outputs ($E_{ON}$, $E_{OFF}$ and I) are available at all times. It should be apparent to those skilled in the art that a separate and additional voltage detector circuit could be connected between the reference electrode terminal 34 and the pipe terminal 44 for detecting the pipe/reference voltage, $E_{ON}$, and it could be connected to the sample and hold circuit 50. However, instead the circuit may be simplified and the additional voltage detector circuit avoided by recognizing that, when the interrupter switch 42 is closed to permit current flow through the zero resistance current detector circuit 40, the pipe terminal 44 is essentially short circuited to the coupon 36 and consequently the voltage appearing at the input to the voltage detector circuit 32 in this state is the pipe/reference voltage. However, when the current through the zero resistance current detector circuit 40 is interrupted by interrupter switch 42, then the input to the voltage detector circuit 32 is the coupon/reference voltage, $E_{OFF}$. This permits the single voltage detector 32 to be used with two separate sample and hold circuits 38 and 50 for respectively sampling both $E_{OFF}$ and $E_{ON}$.

Figure 10:
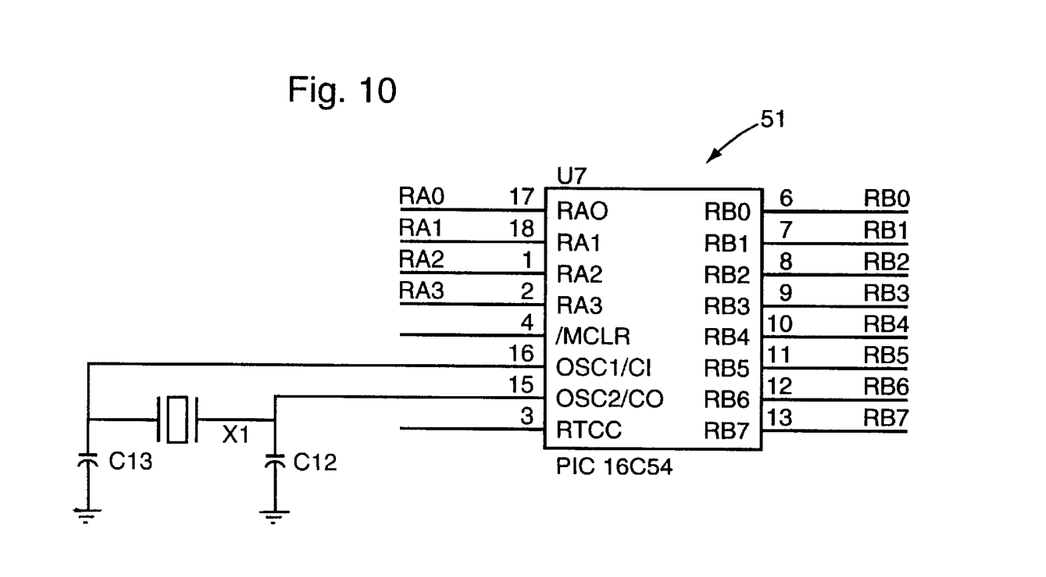

A microprocessor controller 51, illustrated in more detail in FIG. 10, is crystal controlled and has outputs connected to the sample and hold circuits 38, 48, 50 and 42 for switching them between their sampling state and holding state and controlling timing of current interruption.

The details of the preferred circuitry are illustrated in FIGS. 3–10 with specific component identification shown in Table 2. FIGS. 3A and 3B are connected at their edges by the conventional symbology of arrows on the edge of FIG. 3A and interfitting negative arrows on the corresponding edge of FIG. 3B.

Figure 3A:
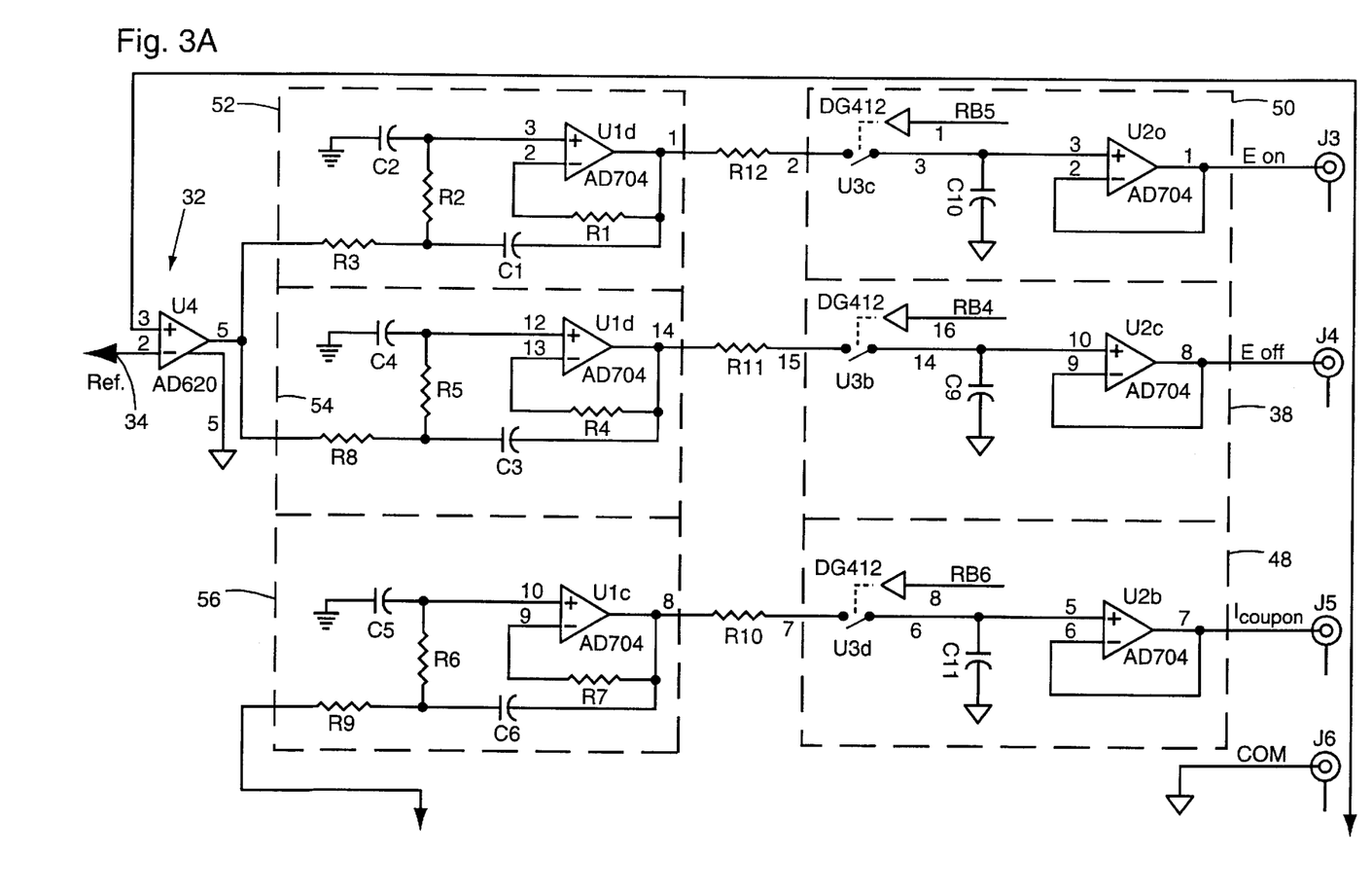
FIGS. 3A and 3B are a schematic diagram illustrating the details of the principal circuitry of the preferred embodiment of the invention.
Figure 3B:
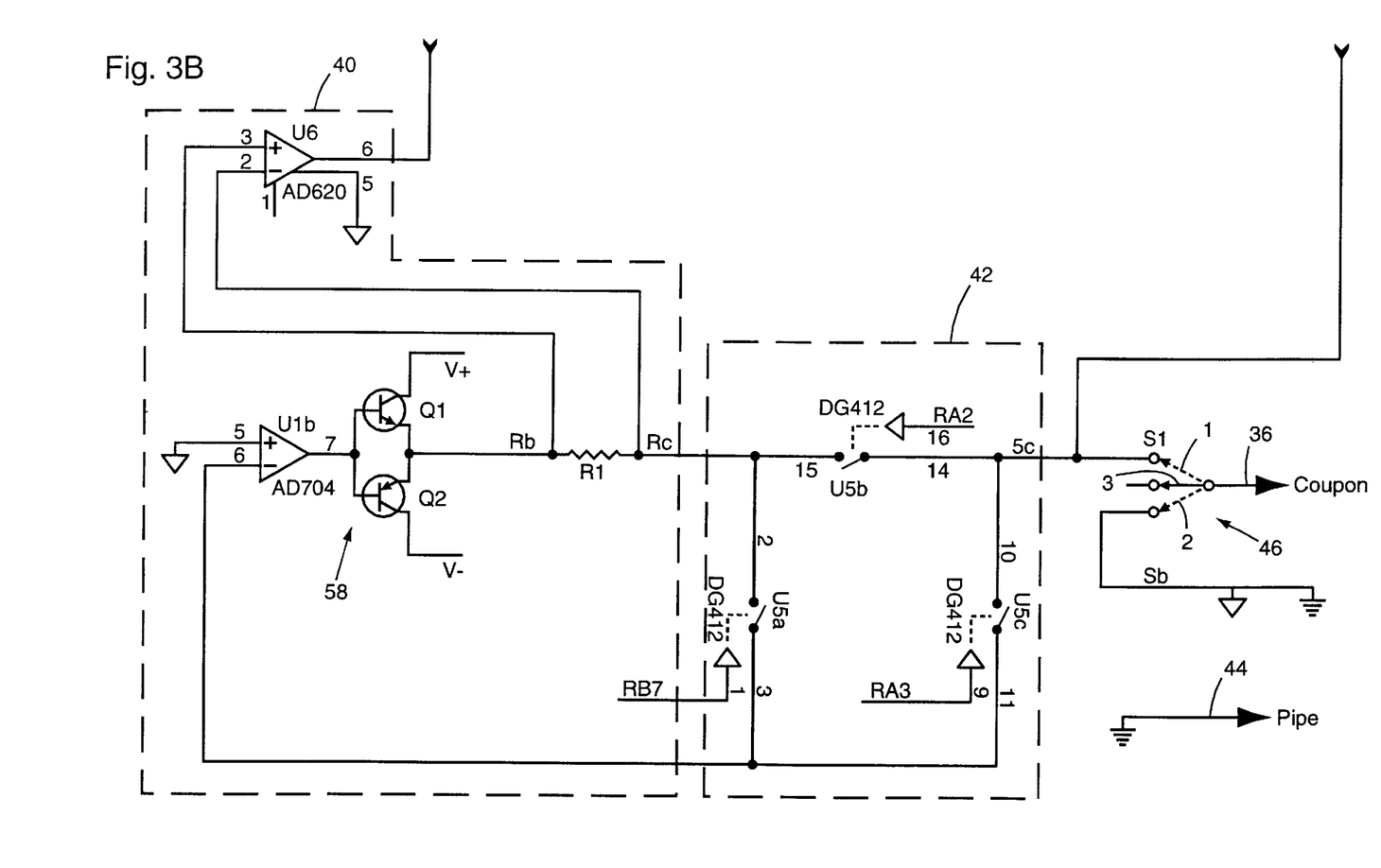

Referring to FIG. 3A and FIG. 3B, the voltage detector 32 has a differential amplifier U4 and is connected through a low pass, active filter circuit 52 to the sample and hold circuit 50. Similarly, the output at pin 6 of the voltage detector circuit 32 is also applied through a low pass, active filter 54 to the sample and hold circuit 38. The mode selection switch 46 is connected from the coupon terminal 36 through the interrupter switch 42 and through the current detector circuit 40 to the pipe. The output from the current detector circuit 40 is similarly applied through a low pass filter 56 to the sample and hold circuit 48. Each of the low pass filter circuits 52, 54 and 56 is an analog active filter having a pass band with a cut off at substantially 10 Hz. The pass band could also extend alternatively to other similar low frequencies, such as 5 Hz or 1 Hz. The low pass filter eliminates the effects of periodic AC variations generated by the cathodic protection system and stray currents.

The current interrupter switch 42 comprises three pi-configured switches. These switches are a bridging switch U5b and switches U5a and U5c which are legs of the pi configured switches. The current detector circuit 40 includes an op amp U1b having its non-inverting input connected through common and ground to the pipe terminal 44 and its inverting input connected through the interrupter switch 42 and the mode selector switch 46 to the coupon terminal 36. The op amp U1b provides a high input impedance first amplifier stage having an output driving a second power amplifier stage 58, comprising transistors Q1 and Q2. The current output of the power amplifier 58 flows through a current sensing resistor R1 so that the output current of the power amplifier 58 flows through both R1 and switch U5b to the coupon terminal 36.

Figure 4:
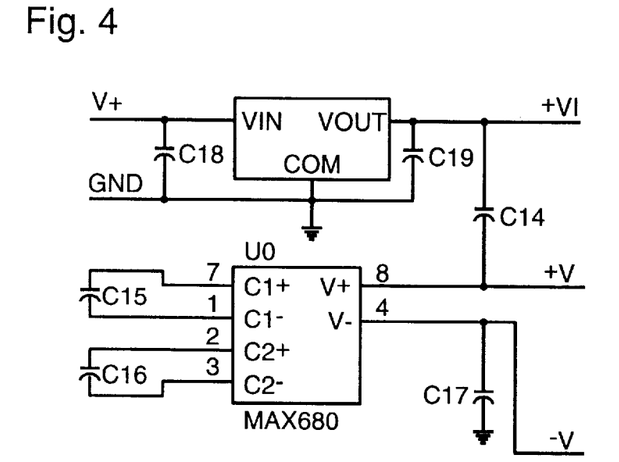
FIGS. 4–10 are schematic diagrams of additional components of the preferred embodiment of the invention.
Figure 5:
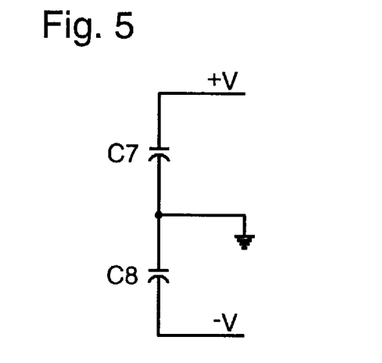

Therefore, the voltage difference between the coupon and pipe is applied to the inputs of the operational amplifier U1b. A continuous current path exist from the coupon through switch U5b, resistor R1, the power amplifier circuit 58, and the power supply for the power amplifier circuit 58 to the pipe. That power supply is illustrated in FIG. 4, and its filter capacitors are illustrated in FIG. 5. As known to those skilled in the art, the operational amplifier U1b has a very high gain and has essentially zero voltage difference between its inverting and non-inverting inputs. Consequently, the current detecting circuit 40, when connected by interrupting switch 42 between the coupon and the pipe, operates as a negative feedback control system in which the power amplifier 58 and its power supply drive sufficient current between the coupon and pipe to maintain the pipe/coupon voltage, which is applied to the inputs to differential amplifier U1b, at essentially zero volts. Since the coupon/pipe voltage is maintained at zero regardless of the current through it, the current detector circuit 40 provides an apparent zero resistance short circuit between the coupon and pipe, with the current through R1 being the coupon-pipe current. The voltage across the resistor R1 is directly proportional to the coupon-pipe current through resistor R1. That voltage is applied through differential amplifier U6 to the low pass filter 56 and the sample and hold circuit 48 to represent the coupon-pipe current.

Three sample and hold switches, U3a, U3b, and U3d, as well as the three switches U5a, U5b, and U5c, forming the interrupter switch 42, are each connected to the micro controller 51 illustrated in FIG. 10. The micro controller cycles the states of these six switches through a sequence of six states which are periodically repeated and are illustrated in Table 1.

Amplifiers U2a, U2b, and U2c, which form a part of the sample and hold circuits 38, 48 and 50, are impedance transforming or isolating amplifiers providing a DC output at output jacks J3, J4, and J5, which is proportional to the voltages of capacitors C9, C10, and C11 at their inputs without draining any significant charge from those capacitors. The op amps U2a, U2b, and U2c, are selected to have an ultra-low droop rate preferably on the order of 0.1 millivolt per second. This prevents any significant discharge of the voltage level maintained on capacitors C9, C10, and C11 as a sample, despite the use of very low update frequencies, typically substantially less than 0.1 Hz.

FIGS. 4–10 illustrate components which are connected to the circuitry of FIGS. 3A and 3B with connected terminal ends of conductors being associated by corresponding labels. FIG. 4 illustrates the power supply circuit for the present invention which utilizes a dual charge pump voltage converter U0. It is connected to the correspondingly labeled connections of FIGS. 3A and 3B.

FIG. 5 illustrates power supply capacitors for the conventional purpose of smoothing the supply voltages and preventing any spikes. These are connected to correspondingly labeled terminals of FIGS. 3A and 3B.

Figure 6:
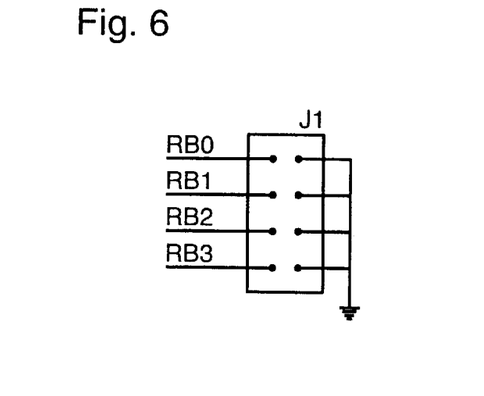

FIG. 6 illustrates connector or jack J1 and its connection to correspondingly labeled conductors in the other figures, including the connections to the microprocessor illustrated in FIG. 10 with correspondingly labeled conductors.

Figure 7:
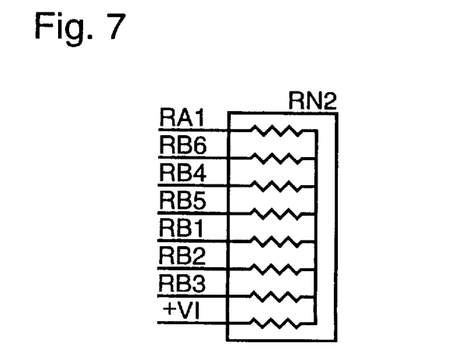

FIG. 7 illustrates the resistor network RN2, labeled to illustrate its connection to the other circuitry.

Figure 8:
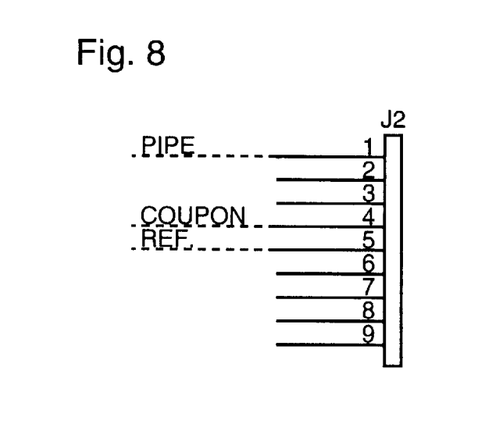

FIG. 8 illustrates the connections to connector or jack J2.

Figure 9:
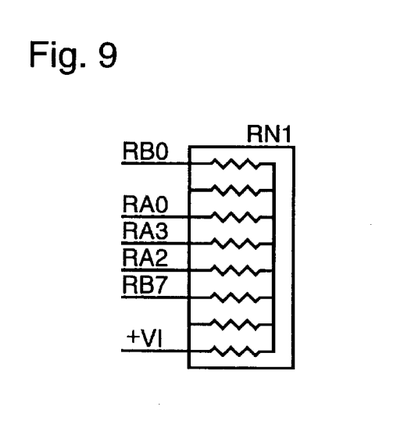

FIG. 9 illustrates resistor network RN1 and the connection to correspondingly labeled conductors of the microprocessor of FIG. 10.

FIG. 10 illustrates the microprocessor 51 and its connections by correspondingly labeled conductors to the circuit elements illustrated in FIGS. 3A, 3B and 6–9.

Turning to the operation of the embodiment illustrated in FIGS. 3–10, Table 1 is a truth table showing the states of these six switches.

TABLE 1

| State and Time | U3a | U3b | U3d | U5a | U5b | U5c |
|---|---|---|---|---|---|---|
| | (O is open, C is closed) | | | | | |
| 1. Equilibrium<br>10 Seconds | O | O | O | O | C | C |
| 2. Sample $E_{ON}$ and Pipe-Coupon Current<br>100 milliseconds | C | O | C | O | C | C |
| 3. Hold Samples At End of State 2<br>100 milliseconds | O | O | O | O | C | C |
| 4. Interrupt Pipe-Coupon Current<br>100 milliseconds | O | O | O | C | O | O |
| 5. Sample $E_{OFF}$ (current interrupted)<br>100 milliseconds | O | C | O | C | O | O |

TABLE 1-continued

| State and Time | U3a | U3b | U3d | U5a | U5b | U5c |
|---|---|---|---|---|---|---|
| | | | (O is open, C is closed) | | | |
| 6. Hold E$_{OFF}$ Value At End Of State 5 (current interrupted) 0.5–1 second Return to State 1. | O | O | O | C | O | O |

In state 1, switches U5b and U5c are closed and consequently current flows through resistor R1 between the coupon and the pipe. State 1 continues for a time interval which is considerably longer than the other states and is typically 10 seconds so that the entire system comes into equilibrium and the coupon is maintained in the same electrical state as the pipe for a time period which is considerably longer than the time period during which measurements are taken. This assures that the measurement intervals are considerably shorter than the time intervals of state 1 so that the measurements will not themselves cause the coupon to experience different conditions than the pipe and thereby introduce an error into the measurements. During the interval of state 1, no measurements are taken.

The microprocessor control then switches to state 2 by closing the sample and hold switches U3a and U3d. State 2 provides an updated sample of the pipe/reference voltage, E$_{ON}$, and the coupon-pipe current I. State 2 is maintained for an interval, of, for example, 100 milliseconds to allow the capacitors C10 and C11 to charge through the coupling resistors R12 and R10. The coupling resistors R10 and R12 are chosen to have a value which is an engineering compromise to provide a sufficiently high resistance which prevents generation of a current surge or spike when the switches U3 are closed, but a sufficiently small resistance to permit the capacitors C9–C11 to charge fully within the time interval of state 2 or state 5.

The micro controller then switches the circuit to state 3 by opening switches U3a and U3d. This holds the samples taken in state 2, resulting in the application of continuous DC level output voltages at output jacks J3 and J5 during all subsequent states, representing E$_{ON}$ and I. In the preferred embodiment, state 3 also lasts for substantially 100 milliseconds.

The micro controller then switches to state 4 in which switches U5b and U5c are opened and switch U5a is closed. State 4 consequently interrupts the coupon-pipe current. Switch U5a is closed in order to provide feedback to the op amp U1b to maintain its stability so that it does not oscillate. No measurement is taken in state 4. However, the duration of state 4, which in the preferred embodiment is 100 milliseconds, provides a portion of the time delay from the interruption of the current to the measurement of the coupon/reference voltage, E$_{OFF}$, commonly referred to as "instant OFF".

The micro controller then switches to state 5 in which the switch U3b is closed to initiate sampling of the reference/ coupon voltage, E$_{OFF}$, under the continued condition of interrupted current. In the preferred embodiment, state 5 continues for 100 milliseconds and then the micro controller switches the circuit to state 6.

In state 6, switch U3b is opened so that the voltage on capacitor C9 is then held and represents E$_{OFF}$. State 6 continues for a total of preferably 0.5 to 1 second. The reason for this time delay is to provide a check during testing, to allow manual readings if desired and to allow adjustable interruption period timing.

After the time interval of state 6, the micro controller 51 then returns the circuit to state 1, and the cycle is periodically repeated.

The sum total of the time durations of states 4 and 5 represents the time interval from current interruption to the measurement of E$_{OFF}$. It is desirable that the micro controller be programmable, such as by appropriate jumpers, so that this total time interval can be programmably selected. This allows each user to select the user's preferred time delay following current interruption until E$_{OFF}$ is measured. For example, the microcontroller circuit is desirably configured to permit selection of a total delay of 100, 200, 300, 400, or 500 milliseconds after the initiation of state 4.

The reason for the pi configuration of the interrupter switch 42 arises from the fact that the switches U5, like the switches U3, are all CMOS analog switches controlled by the micro controller 51. If they had zero resistance, then switch U5c would be unnecessary. However, CMOS analog switches typically have a resistance when closed of approximately 50 ohms. Consequently, if switch U5c were omitted, the voltage applied to the input of differential amplifier U1b, the voltage which the circuit maintains at essentially zero, would not be the coupon/pipe voltage, but would be offset from that voltage by the IR drop through switch U5b, caused by the significant pipe/coupon current. Therefore, switch U5c, which carries essentially no current, assures that the coupon voltage itself is accurately input to the differential amplifier U1b.

As a result of the operation of the circuit of the present invention, the DC voltages maintained at output jacks J3, J4, and J5 continuously represent E$_{ON}$, E$_{OFF}$, and I, and these values are updated periodically, for example every 11–12 seconds. Because these are simple DC values, they may be read using a digital multimeter. This permits an untrained person to connect the multimeter probes between grounded terminal J6, and in turn each of the terminals J3, J4, and J5, and to simply read a number from the digital multimeter and manually record the number. Alternatively, or additionally, the DC output levels at the jacks can be recorded by a data acquisition and storage system, or data logger, in sequential, selected intervals over a substantial period of time. These data can then be periodically, locally read or transmitted to a remote location.

TABLE 2

| Part | Description | Value |
|---|---|---|
| C1, C3, C6, C9, C10, C11 | Polypropylene X7R Capacitor | 1 uf |
| C2, C4, C5 | Polypropylene X7R Capacitor | .47 uf |
| C7, C8, C18, C19 | Tantalum Capacitor | .1 uf |
| C12, C13 | Ceramic Disc Capacitor | 12 pf |
| C14, C15, C16, C17 | Tantalum Capacitor | 4.7 uf |
| R1, R4, R7 | 1% Precision ¼ Watt Resistor | 44K |
| R2, R3, R5, R6, R8, R9 | 1% Precision ¼ Watt Resistor | 22.1K |
| R10, R11, R12 | 5% ¼ Watt Resistor | 330 ohm |
| U0 | Dual Charge Pump Voltage Converter | Max 680 |
| U1, U2 | 4 Picoampere Input Current Bipolar Op Amp | AD704 |
| U3, U5 | Monolithic Quad SPDT CMOS Analog Switch | DG412 |
| U4, U6 | Low Power Instrumental Amplifier | AD620AN |

TABLE 2-continued

| Part | Description | Value |
| --- | --- | --- |
| U7 | Programmable Micro Controller | Pic16C56 |
| Q1 | NPN Transistor | PN2222A |
| Q2 | PNP Transistor | PN2907A |
| Z1 | Crystal Oscillator | 32.768 Khz |
| Rn1, Rn2 | Resistor Array | 10K |
| J1 | 8 Pin Jumper | Jumper |
| Q3 | 4 Volt Low Dropout Regulator | 711 Reg |

While certain preferred embodiments of the present invention have been disclosed in detail, it is to be understood that various modifications may be adopted without departing from the spirit of the invention or scope of the following claims.

What is claimed is:

1. A circuit for monitoring electrical parameters associated with a buried metal object, a coupon and a reference electrode in a soil, the monitoring circuit comprising:

(a) a voltage detector circuit having an input connected between the reference electrode and the coupon and an output having a magnitude representing the voltage at its input;

(b) a current detector circuit having an input connected between the object and the coupon and an output having a magnitude representing the object-coupon current;

(c) at least one sample and hold circuit connected to at least one of the outputs for sampling and storing at least one of the outputs; and (d) a control circuit for periodically actuating the sample and hold circuit.

2. A monitoring circuit in accordance with claim 1, wherein a current interrupter switch is interposed in series with the current detector circuit and connected to the control circuit for periodically interrupting the current through the current detecting circuit and wherein the current detector circuit has a substantially zero input resistance.

3. A monitoring circuit in accordance with claim 2 and further comprising second and third sample and hold circuits connected to the control circuit, one sample and hold circuit connected to the output of the current detector circuit for periodically sampling and storing the output of the current detector circuit and the second and third sample and hold circuits connected to the output of the voltage detector circuit for periodically sampling and storing the output of the voltage detector circuit.

4. A monitoring circuit in accordance with claim 1 or claim 2 or claim 3 and further comprising a low pass filter interposed between each detector circuit and the sample and hold circuit connected to its output.

5. A monitoring circuit in accordance with claim 4 wherein the low pass filter is an analog active filter having a pass band below substantially 10 Hz.

6. A monitoring circuit in accordance with claim 4 wherein the object is connected to a node and the coupon is connected to another node and wherein the current detector circuit comprises an op-amp input stage having its inputs connected between the coupon node and the object node, a power amplifier stage driven by the op-amp and having a power supply connected between said power amplifier and a first one of said nodes, and a current detecting resistor at times series connected between an output of the power amplifier and the second one of said nodes for at times maintaining substantially zero volts between the object and the coupon.

7. A monitoring circuit in accordance with claim 4 and further comprising a third sample and hold circuit having an input connected to the output of the voltage detector circuit.

8. A monitoring circuit in accordance with claim 4 wherein each sample and hold circuit has a droop rate on the order of substantially 0.1 millivolt per second.

9. A monitoring circuit in accordance with claim 1 wherein:

(a) the current detector circuit has a substantially zero input resistance and comprises an op-amp input stage having its inputs connected between the coupon and the object, a power amplifier stage driven by the op-amp and having a power supply connected between said power amplifier and the object, and a current detecting resistor at times series connected between an output of the power amplifier and the coupon for at times maintaining substantially zero volts between the object and the coupon; and (b) a current interrupter switch is interposed in series between the resistor and the coupon and connected to the control circuit for periodically interrupting the current through the current detecting circuit, the current interrupter switch comprising at least three switches connected in a pi configuration, a bridging one of the three switches connected between the resistor and the coupon, and each leg of the pi configured switches connected to the input of the op-amp which is not connected to the object.

10. A monitoring circuit in accordance with claim 9 and further comprising:

(a) a second sample and hold circuit connected to the control circuit, one sample and hold circuit connected to the output of the current detector circuit for periodically sampling and storing the output of the current detector circuit and the second sample and hold circuit connected to the output of the voltage detector circuit for periodically sampling and storing the output of the voltage detector circuit;

(b) a third sample and hold circuit having an input connected to the output of the voltage detector circuit for periodically sampling and storing the output of the voltage detector circuit; and (c) a low pass filter interposed between each detector circuit and the sample and hold circuit connected to its output.

11. A monitoring circuit in accordance with claim 10 wherein the low pass filter is an analog active filter having a pass band below substantially 10 Hz and wherein each sample and hold circuit has a droop rate on the order of substantially 0.1 millivolt per second.

12. A method for monitoring electrical parameters associated with a buried object, a coupon and a reference electrode in a soil, the method comprising:

(a) detecting, sampling and holding the current, I, through a conductive path connected between the object and the coupon;

(b) opening the circuit through said conductive path to interrupt the object-coupon current; and (c) sampling and holding the voltage, $E_{OFF}$, between the coupon and the reference electrode a selected time interval after interrupting the object-coupon current.

13. A method in accordance with claim 12 and further comprising periodically repeating said method steps.

14. A method in accordance with claim 13 and further comprising periodically maintaining substantially zero volts between the object and the coupon and sampling and storing the voltage, $E_{ON}$, between the coupon and the reference while the coupon-object voltage is substantially zero volts to obtain the voltage between the reference and the object.

15. A method in accordance with claim 12 or claim 13 or claim 14 wherein the object-coupon voltage is maintained at substantially zero by supplying sufficient current from a power amplifier circuit through a current detecting resistor connected in series with the conductive path.

16. A method in accordance with claim 15 and further comprising periodically reading the values of I, $E_{OFF}$ and $E_{ON}$ by with a digital multimeter.

17. A method in accordance with claim 15 and further comprising storing a sequence of the stored values of I, $E_{OFF}$ and $E_{ON}$ for subsequent transfer and storage.

18. A method in accordance with claim 14 and further comprising periodically reading the values of I, $E_{OFF}$, and $E_{ON}$ by with a digital multimeter.

19. A method in accordance with claim 14 and further comprising storing a sequence of the stored values of I, $E_{OFF}$ and $E_{ON}$ for subsequent transfer and storage.

20. A method in accordance with claim 14 and further comprising maintaining substantially zero volts between the coupon and object for a time interval which is at least a multiple of ten times the time interval during which the object-coupon current is interrupted.

* * * * *